United States Patent
Hunt et al.

(10) Patent No.: US 6,358,268 B1
(45) Date of Patent: Mar. 19, 2002

(54) SURGICAL INSTRUMENT

(75) Inventors: Robert B. Hunt, 129 Dedham St., Dover, MA (US) 02030; Gerald S. Melsky, Lexington; Stephen C. Evans, Westford, both of MA (US)

(73) Assignee: Robert B. Hunt, Dover, MA (US)

( * ) Notice: Subject to any disclaimer, the term of this patent is extended or adjusted under 35 U.S.C. 154(b) by 0 days.

(21) Appl. No.: 09/519,103

(22) Filed: Mar. 6, 2000

(51) Int. Cl.$^7$ ............................................. A61B 17/28
(52) U.S. Cl. ...................................... 606/206; 606/207
(58) Field of Search ................................. 606/205–210, 606/170, 171, 174, 167, 138, 139, 151; 128/751, 752, 749

(56) References Cited

U.S. PATENT DOCUMENTS

| | | |
|---|---|---|
| 3,894,336 A | 7/1975 | Desimone |
| 4,164,225 A | 8/1979 | Johnson et al. |
| 5,071,419 A | 12/1991 | Rydell et al. |
| 5,163,942 A | 11/1992 | Rydell |
| 5,171,258 A | 12/1992 | Bales et al. |
| 5,171,311 A | 12/1992 | Rydell et al. |
| 5,192,280 A | 3/1993 | Parins |
| 5,197,963 A | 3/1993 | Parins |
| 5,207,213 A | 5/1993 | Auhll et al. |
| 5,217,458 A | 6/1993 | Parins |
| 5,250,047 A | 10/1993 | Rydell |
| 5,258,006 A | 11/1993 | Rydell et al. |
| 5,269,754 A | 12/1993 | Rydell |
| 5,304,147 A | 4/1994 | Johnson et al. |
| 5,312,434 A | 5/1994 | Crainich |
| 5,320,636 A | 6/1994 | Slater |
| 5,330,471 A | 7/1994 | Eggers |
| 5,334,198 A | 8/1994 | Hart et al. |
| 5,342,359 A | 8/1994 | Rydell |
| 5,342,381 A | 8/1994 | Tidemand |
| 5,352,222 A | 10/1994 | Rydell |
| 5,356,408 A | 10/1994 | Rydell |
| 5,360,428 A | 11/1994 | Hutchinson, Jr. |
| 5,383,888 A | 1/1995 | Zvenyatsky et al. |
| 5,391,166 A | 2/1995 | Eggers |
| 5,403,312 A | 4/1995 | Yates et al. |
| 5,403,332 A | 4/1995 | Christoudias |
| 5,445,638 A | 8/1995 | Rydell et al. |
| 5,456,684 A | 10/1995 | Schmidt et al. |
| 5,462,546 A | 10/1995 | Rydell |
| 5,478,347 A | 12/1995 | Aranyi |
| 5,480,409 A | 1/1996 | Riza |
| 5,496,317 A | 3/1996 | Goble et al. |
| 5,514,134 A | 5/1996 | Rydell et al. |
| 5,522,830 A | 6/1996 | Aranyi |
| 5,527,313 A | 6/1996 | Scott et al. |
| 5,531,744 A | 7/1996 | Nardella et al. |
| 5,540,685 A | 7/1996 | Parins et al. |
| 5,569,164 A | 10/1996 | Lurz |
| 5,569,243 A | 10/1996 | Kortenbach et al. |
| 5,569,843 A | 10/1996 | Kortenbach et al. |

(List continued on next page.)

FOREIGN PATENT DOCUMENTS

| | | |
|---|---|---|
| DE | 198 33 600 A1 | 7/1998 |
| WO | PCT/US88/03306 | 9/1988 |
| WO | PCT/US96/08263 | 6/1995 |
| WO | PCT/US96/18423 | 11/1996 |
| WO | PCT/US98/15582 | 7/1998 |

*Primary Examiner*—Kevin Truong
(74) *Attorney, Agent, or Firm*—Kirk Teska; Iandiorio & Teska

(57) ABSTRACT

A surgical instrument including a handle assembly; a shaft connected on one end to the handle assembly; and an end assembly extending from the other end of the shaft. The end assembly is constructed to include a fixed member including on one portion thereof a fixed scissor blade and on another portion thereof a fixed forcep jaw. The end assembly also includes a pivotable scissor blade for cutting tissue between the fixed scissor blade and the pivotable scissor blade and a pivotable forcep jaw for grasping tissue between the fixed forcep jaw and the pivotable forcep jaw.

17 Claims, 9 Drawing Sheets

U.S. PATENT DOCUMENTS

| | | | |
|---|---|---|---|
| 5,571,100 A | | 11/1996 | Goble et al. |
| 5,573,535 A | | 11/1996 | Viklund |
| 5,578,052 A | | 11/1996 | Koros et al. |
| 5,599,350 A | | 2/1997 | Schulze et al. |
| 5,603,711 A | | 2/1997 | Parins et al. |
| 5,603,723 A | | 2/1997 | Aranyi et al. |
| 5,637,110 A | | 6/1997 | Pennbacker et al. |
| 5,647,840 A | | 7/1997 | D'Amelio et al. |
| 5,658,281 A | | 8/1997 | Heard |
| 5,665,100 A | * | 9/1997 | Yoon .......................... 606/139 |
| 5,674,220 A | | 10/1997 | Fox et al. |
| 5,735,849 A | * | 4/1998 | Baden et al. ................ 606/205 |
| 5,741,285 A | | 4/1998 | McBrayer et al. |
| 5,743,906 A | | 4/1998 | Parins et al. |
| 5,752,951 A | | 5/1998 | Yanik |
| 5,766,166 A | | 6/1998 | Hooven |
| 5,779,701 A | | 7/1998 | McBrayer et al. |
| 5,797,927 A | | 8/1998 | Yoon |
| 5,797,941 A | | 8/1998 | Schulze et al. |
| 5,827,281 A | | 10/1998 | Levin |
| 5,833,690 A | | 11/1998 | Yates et al. |
| 5,851,214 A | | 12/1998 | Larsen et al. |
| 5,893,875 A | | 4/1999 | O'Connor et al. |
| 5,895,370 A | | 4/1999 | Edwards et al. |
| 5,906,629 A | | 5/1999 | Oren et al. |
| 5,908,420 A | | 6/1999 | Parins et al. |
| 6,022,334 A | | 2/2000 | Edwards et al. |
| 6,074,408 A | | 6/2000 | Freeman |
| RE36,795 E | | 7/2000 | Rydell |
| 6,190,386 B1 | | 2/2001 | Rydell |

* cited by examiner

SURGICAL INSTRUMENT

FIELD OF INVENTION

This invention relates to a surgical instrument and more particularly to a combined laparoscopic scissors and forceps device.

BACKGROUND OF INVENTION

Laparoscopic surgery is used to provide a wide variety of surgical procedures on a patient's abdomen. The application of laparoscopic methods continues to grow as techniques are refined and the associated surgical instruments are improved. Patients benefit from laparoscopic procedures because the methods employed minimize the amount of trauma associated with a given procedure. Hence, patient survival is enhanced and recovery times are decreased.

Prior art laparoscopic surgical instruments typically include a handle, a 33 centimeter length, 5 millimeter diameter shaft which can be inserted through a cannula placed in a patient's abdominal wall, and scissors or tissue grasping jaws (e.g., forceps) extending from the end of the shaft.

In some cases, laparoscopic graspers, and/or scissors and some other types of instruments have the ability to apply RF energy in order to locally vaporize tissue and thereby cut through it or to coagulate blood vessels. There are two common ways in which the RF energy is applied. In either method, current travels between two electrodes. In monopolar instruments, the surgical instrument serves as one electrode and the second electrode is a large surface area electrode placed on the patient. In bipolar instruments, both electrodes are disposed on the surgical instrument in close proximity to one another.

Many conventional laparoscopic surgical instruments tend to be clumsier than those used in conventional surgery. As explained above, in laparoscopic surgery, the surgical instruments are inserted through a cannula placed in the patient's abdominal wall. To keep patient trauma to a minimum, only a limited number of cannula are employed for a given procedure. Often, using existing surgical instruments, the instruments must be repeatedly removed from the cannula and replaced with different instruments and removed and replaced again. This process of repeated instrument exchanges greatly increases the time it takes to perform a given medical procedure.

Two commonly used laparoscopic instruments are scissors and tissue graspers. Scissors are used to dissect tissue, transect ligated vessels or other bodily ducts (such as fallopian tubes), trim sutures and ligatures and to perform other cutting functions. Graspers or forceps are used to grip and manipulate tissue and to perform a variety of blunt dissecting procedures. Tissue is either grasped and pulled away from substrate tissue to which it is loosely connected or the blunt tips of the closed graspers are inserted between loosely connected tissue strata and then the tips are forced apart separating the tissue strata. The operation of ordinary scissors and forceps is very familiar to surgeons and non-medical personnel alike and their function and operation are somewhat intuitive. This fact remains true when scissors or forceps are incorporated into a traditional laparoscopic instrument.

Traditionally, when tissue cutting procedures are required, a scissors type laparoscopic instrument is used. When tissue grasping procedures are required, a forceps type laparoscopic instrument is used. Thus, the surgeon must either employ two cannulas or switch instruments depending on whether cutting or grasping procedures are required.

To overcome this problem, those skilled in the art have developed surgical instruments with detachable scissors and forceps end assemblies, and surgical instruments with combined scissors and forceps end assemblies.

For example, U.S. Pat. No. 5,893,875 discloses a surgical instrument with replaceable end effector assemblies. To switch between tissue cutting and grasping procedures, however, the surgeon must withdraw the instrument from the patient and replace the scissors end effector assembly with a forceps end effector assembly.

This practice of instrument exchange greatly increases the time it takes to complete a given surgical procedure. An attempt to overcome this problem is disclosed by a combined cutting blade/forceps end assembly. Pivoting jaws 10 and 12, FIG. 1, are configured as forceps and blade 14 attached to pivoting jaw 10 allows the surgeon to cut the tissue. See U.S. Pat. No. 5,456,684. In another prior art device, one portion of each operable jaw 20, 22, FIG. 2, includes scissors portions 24, 24' and a forceps portions 26, 26', respectively. See U.S. Pat. No. 5,908,420.

In another prior art device, cutting blade 30, FIG. 3, is extendable between forceps 32 and 34. See U.S. Pat. No. 5,496,317. In still another device, blade 40, FIG. 4 is disposed between forceps 42 and 44. See U.S. Pat. No. 5,573,535. See also the BiCoag® bipolar cutting forceps available from Everest Medical, 13755 First Avenue North, Minneapolis, Minn. 55441-5454.

All of these devices suffer from the fact that the scissoring and grasping capabilities are poorer than that which is available separately in single function devices.

Moreover, surgeons will not generally use any surgical instrument which does not operate in the way expected or in a way which is not intuitive. When conventional surgical devices with scissor grips are used, it is expected that the action of closing the scissor grips closes the scissor blades for tissue cutting or brings the forceps jaws together to grasp the tissue between them. This is not the case with the device discussed above. For example, in order to use the device disclosed in U.S. Pat. No. 5,573,535, the surgeon uses a scissor grip to operate the forceps jaws but must operate a separate lever to effect distal movement of the blade member to cut tissue. See the '535 patent, col. 5, lines 43–66.

Other shortcomings of prior art devices include their complexity and high manufacturing costs. High manufacturing costs are especially important in surgical devices because they are often used in connection with one procedure on a given patient and then discarded.

BRIEF SUMMARY OF THE INVENTION

It is therefore an object of this invention to provide a surgical instrument with an end assembly which includes both a pivoting scissor blade and a pivoting forceps jaw.

It is a further object of this invention to provide such a surgical instrument which eliminates the need for the surgeon to switch instruments during a given medical procedure.

It is a further object of this invention to provide such a surgical instrument which eliminates the need for additional cannulas inserted through a patient's abdominal wall.

It is a further object of this invention to provide such a surgical instrument in which the scissoring and the grasping capabilities are as good as that which is available separately in single function devices.

It is a further object of this invention to provide such a surgical instrument which operates in the way expected and whose use is intuitive.

It is a further object of this invention to provide such a surgical instrument which does not require the surgeon to operate separate levers in order to effect tissue cutting or tissue grasping procedures.

It is a further object of this invention to provide such a surgical instrument which is simple in design and which can be manufactured at a low cost.

It is a further object of this invention to provide such a surgical instrument which allows surgeons to remain focused on the operating procedure and not distracted by instrument exchanges or the need to operate separate levers.

It is a further object of this invention to provide such a surgical instrument which results in medical procedures performed in a shorter period of time.

It is a further object of this invention to provide such a surgical instrument which can be accommodated by a five millimeter cannula.

It is a further object of this invention to provide such a surgical instrument which can be easily and ergonomically operated by one hand. It is a further object of this invention to provide such a surgical instrument which can be equipped with bipolar or monopolar RF energy subsystems for electrosurgical procedures.

It is a further object of this invention to provide such a surgical instrument which can be readily equipped with surgical end effectors other than scissors and tissue graspers.

It is a further object of this invention to provide a surgical instrument with an end effector that may be rotated relative to its handle.

The invention results from the realization that a more intuitive, ergonomic, easier to use, and easier to manufacture surgical instrument which performs both tissue cutting and grasping procedures without the need to replace the end assembly and which incorporates both scissors and forceps (or other end effector combinations) jaws in a single end assembly can be effected by a uniquely configured end assembly with a fixed central member that functions both as a scissor blade and a forcep jaw disposed between a separate pivotable scissor blade and a separate pivotable forcep jaw and by a linkage assembly connected between the end assembly and a pair of scissors grips which allow the surgeon to open and close the scissor blades in one range of motion and to open and close the forceps jaws in another range of motion.

This invention features a surgical instrument comprising a handle assembly, a shaft connected on one end to the handle assembly, and an end assembly extending from the other end of the shaft. The end assembly includes a fixed member including on one portion thereof a fixed scissor blade and on another portion thereof a fixed forcep jaw. The end assembly also includes a pivotable scissor blade for cutting tissue between the fixed scissor blade and the pivotable scissor blade and a pivotable forcep jaw for grasping tissue between the fixed forcep jaw and the pivotable forcep jaw.

The fixed forcep jaw and the pivotable forcep jaw may include serrations thereon. The fixed member is typically disposed between the pivotable scissor blade and the pivotable forcep jaw. In the preferred embodiment, the pivotable scissor blade is disposed above the fixed member and the pivotable forcep jaw is disposed below the fixed member. Thus, the fixed forcep jaw is on a lower portion of the fixed member and the fixed scissor blade is on an upper portion of the fixed member.

The handle assembly preferably includes spaced scissor-like handles. Typically one handle is pivotably attached to the handle assembly and has a predetermined angular range of motion with respect to the handle assembly. The shaft then includes a linkage assembly which opens and closes the scissor blades during one portion of the angular range of motion of the pivoting handle and opens and closes the forcep jaws during a second portion of the angular range of motion of the pivoting handle. In one embodiment, a scissor blade push rod and a forcep jaw push rod are slidably disposed in the shaft. The pivotable scissor blade is pivotably attached on one side of the fixed member and the pivotable forcep jaw is pivotably attached on another side of the fixed member. In a preferred embodiment, the scissor blade push rod is connected on one end to a scissor blade link which is connected to the pivotable scissor blade and the forcep jaw push rod is connected on one end to a forcep jaw link which is connected to the pivotable forcep jaw.

In the preferred embodiment, the scissor blade push rod is connected on one end to a scissor block slidably disposed in the handle assembly. The scissor block includes a projection extending into a first cam groove. The jaw push rod is connected on one end to a jaw block also slidably disposed in the handle assembly. The jaw block includes a projection extending into a second cam groove. The cam grooves are typically formed in an ear of the pivotable handle.

Electrical conductors may be incorporated and connected on one end to the fixed member and the pivotable forcep jaw for coagulating tissue.

The invention also features a surgical device comprising a handle assembly; a shaft connected on one end to the handle assembly; and an end assembly extending from the other end of the shaft, the end assembly including a fixed member including on one section thereof a fixed portion of a first surgical instrument and on another section thereof a fixed portion of a second surgical instrument. The end assembly also includes a pivotable portion of the first surgical instrument pivotably attached to the fixed member and disposed to cooperate with the fixed portion of the first surgical instrument to perform a first type of medical procedure. The end assembly also includes a pivotable portion of the second surgical instrument pivotably attached to the fixed member and disposed to cooperate with the fixed portion of the second surgical instrument to perform a second type of medical procedure.

In one embodiment, the fixed portion of the first surgical instrument is a fixed scissor blade and the pivotable portion of the first surgical instrument is a pivotable scissor blade. Also, the fixed portion of the second surgical instrument may be a fixed forcep jaw and the pivotable portion of the second surgical instrument may be a pivotable forcep jaw.

In another embodiment the handle member includes means to allow rotation of the end assembly and shaft relative to the handle assembly.

An end assembly for a surgical instrument in accordance with this invention features a fixed member including on one portion thereof a fixed scissor blade and on another portion thereof a fixed forcep jaw; a pivotable scissor blade pivotably attached to the fixed member for cutting tissue between the fixed scissor blade and the pivotable scissor blade; and a pivotable forcep jaw pivotably attached to the fixed member for grasping tissue between the fixed forcep jaw and the pivotable forcep jaw.

BRIEF DESCRIPTION OF THE DRAWINGS

Other objects, features and advantages will occur to those skilled in the art from the following description of a preferred embodiment and the accompanying drawings, in which.

PREFERRED EMBODIMENT

Figure 2:
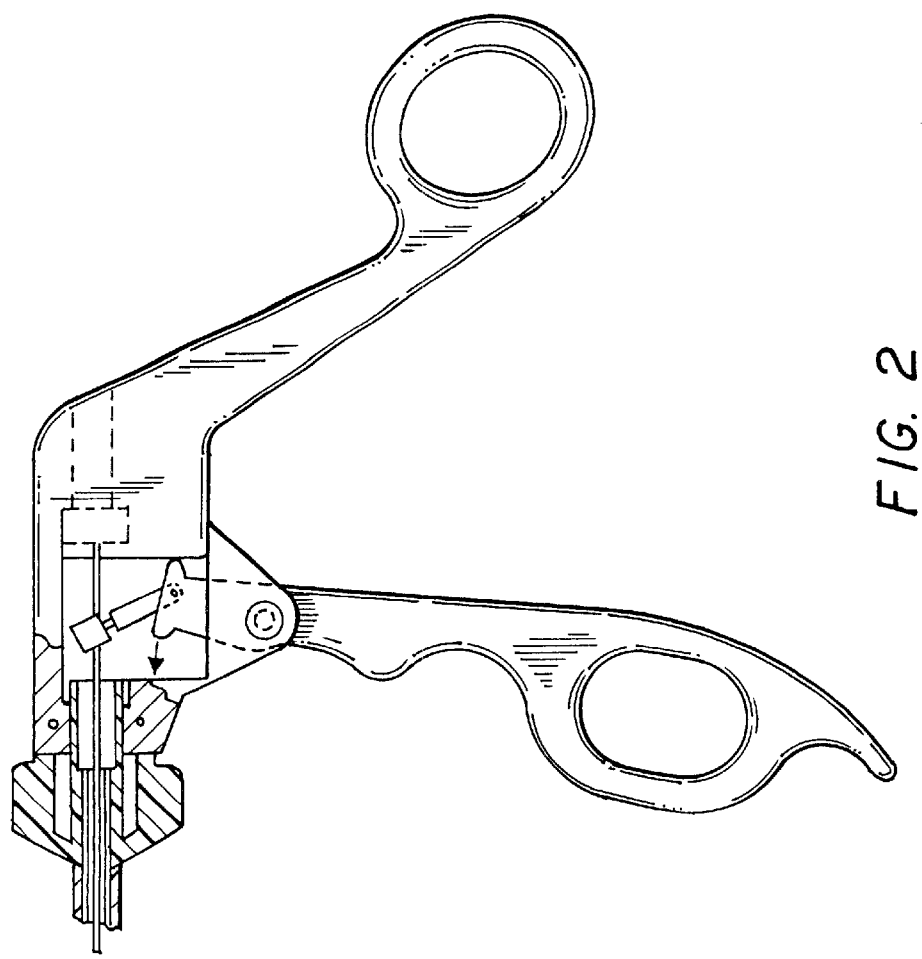
FIG. 2 is a schematic side view of a prior art device which includes operable jaws each of which include both a scissor portion and a forcep portion as disclosed in U.S. Pat. No. 5,908,420.
Figure 1:
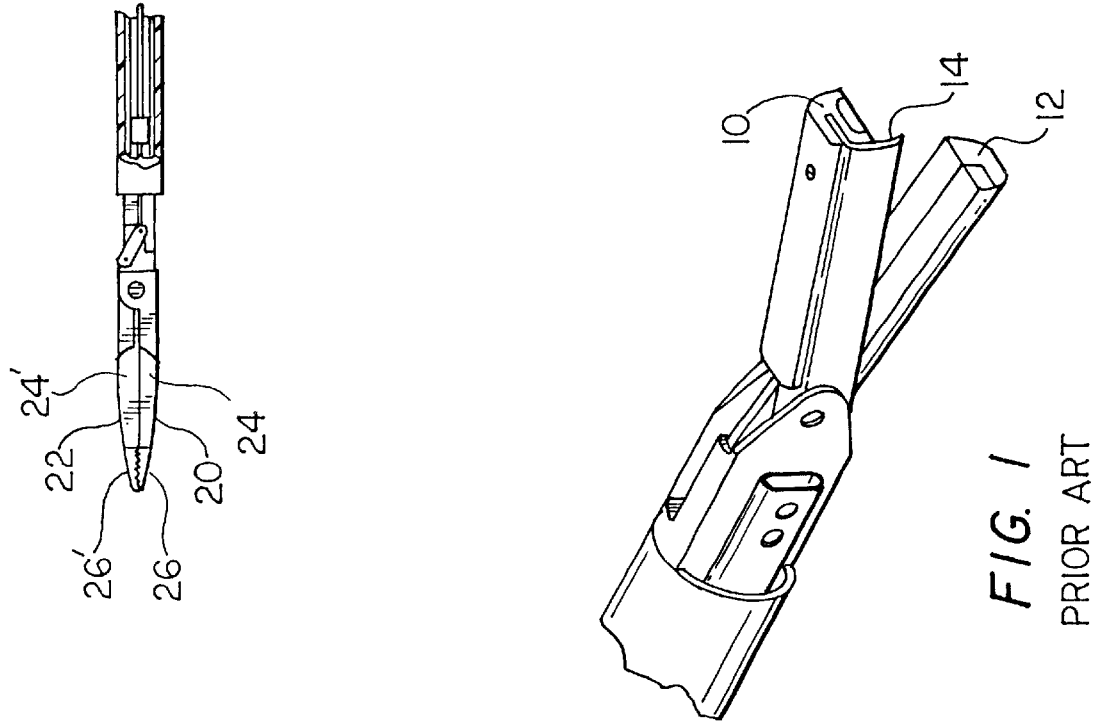
FIG. 1 is a schematic view of a prior art surgical instrument end assembly including a combined cutting blade/forceps tissue grasper device as disclosed in U.S. Pat. No. 5,456,684.
Figures 3, 4:
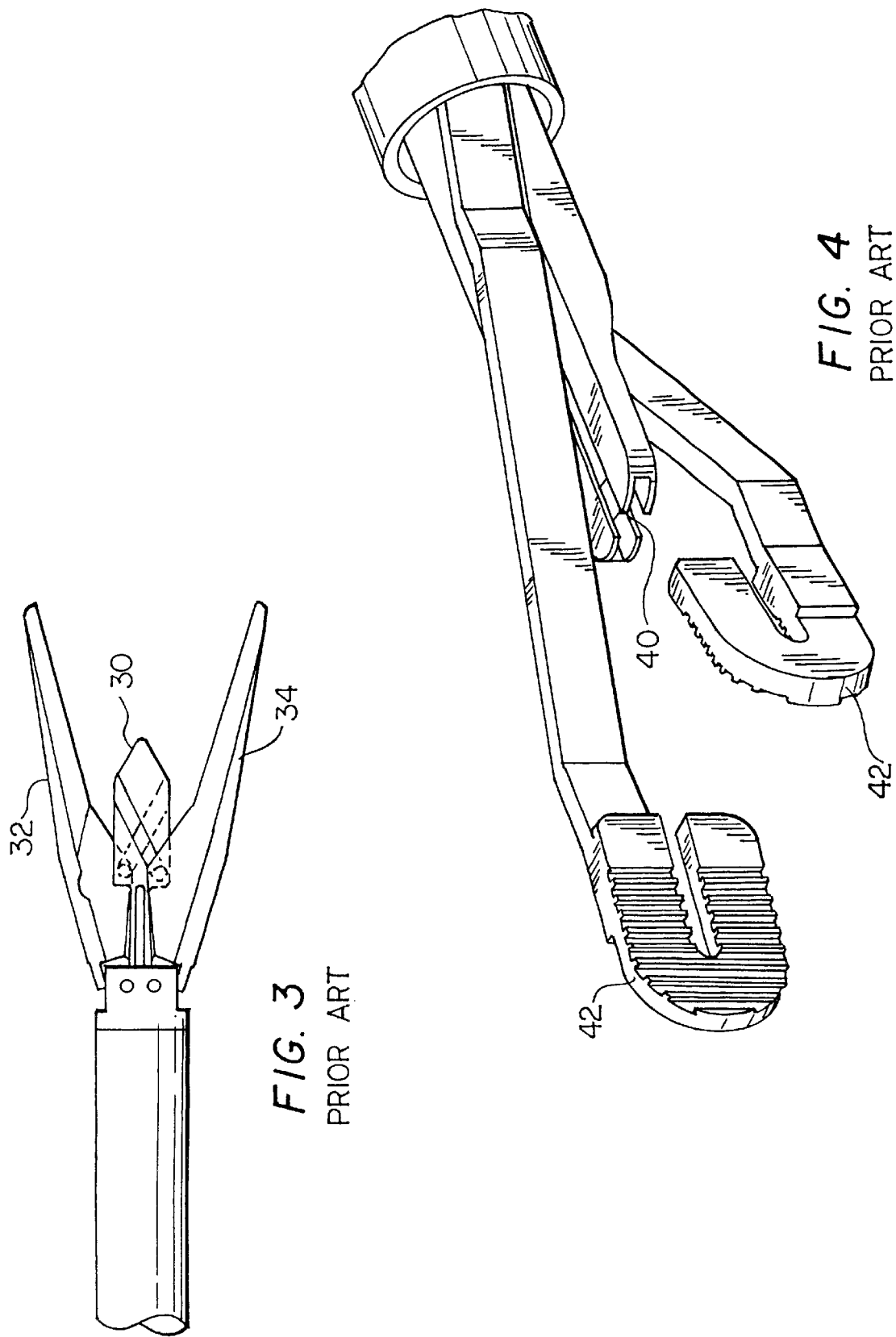
FIG. 3 is a schematic side view of the end assembly of a prior art surgical instrument which includes a cutting blade extendable between spaced forcep jaws as disclosed in U.S. Pat. No. 5,496,317.
FIG. 4 is a schematic view of still another prior art surgical instrument end assembly which includes a blade disposed between opposed forcep jaws as disclosed in U.S. Pat. No. 5,573,535.
Figure 5:
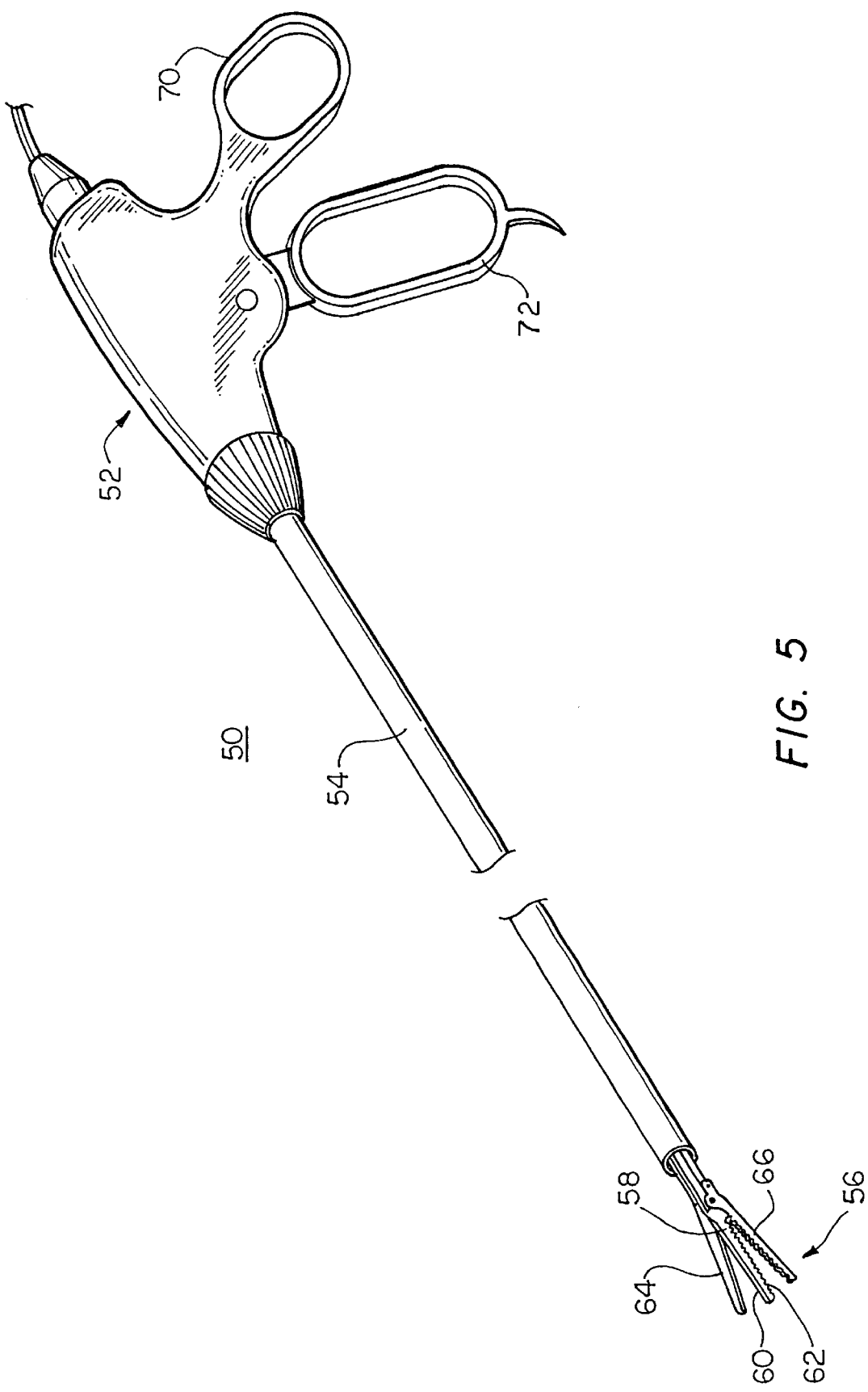
FIG. 5 is a schematic view of the surgical instrument of the subject invention.

Surgical instrument 50, FIG. 5 in accordance with the subject invention is particularly adapted for use in laparoscopic procedures and includes handle assembly 52 with fixed scissor like handle 70 and pivotably attached scissor like handle 72, shaft 54, and end assembly 56 extending from shaft 54. End assembly 56 comprises centrally disposed fixed member 58 which includes both scissor blade 60 and forcep jaw 62. End assembly 56 also includes upper pivotable scissor blade 64 and lower pivotable forcep jaw 66. Thus, end assembly 56 allows the surgeon to perform both tissue cutting procedures, by virtue of scissor blades 60 and 64, and tissue grasping procedures, by virtue of forcep jaws 62 and 66, without withdrawing device 50 from the patient and replacing the end assembly as is the case in certain prior art devices.

Shaft 54 is typically 33 centimeters in length and 5 millimeters in diameter and made of a sterilizable plastic or metal material. End assembly 56 is typically made of stainless surgical steel. Forcep jaws 62 and 66 typically include serrations as shown but could also be smooth in other embodiments. Forcep jaw 62 could also be concave and forcep jaw 66 convex in shape. Also, scissor blades 64 and 60 preferably have blunt tips as shown but in other embodiments could be sharpened. The scissor blades could also each include cutting serrations. In addition, the scissor blades and/or forcep jaws are shown to be straight but could be curved.

In use, scissor blades 60 and 64 and forcep jaws 62 and 66 are typically not both open at the same time as shown in FIG. 5. The configuration shown in FIG. 5 is for illustrative purposes only.

Figure 6:
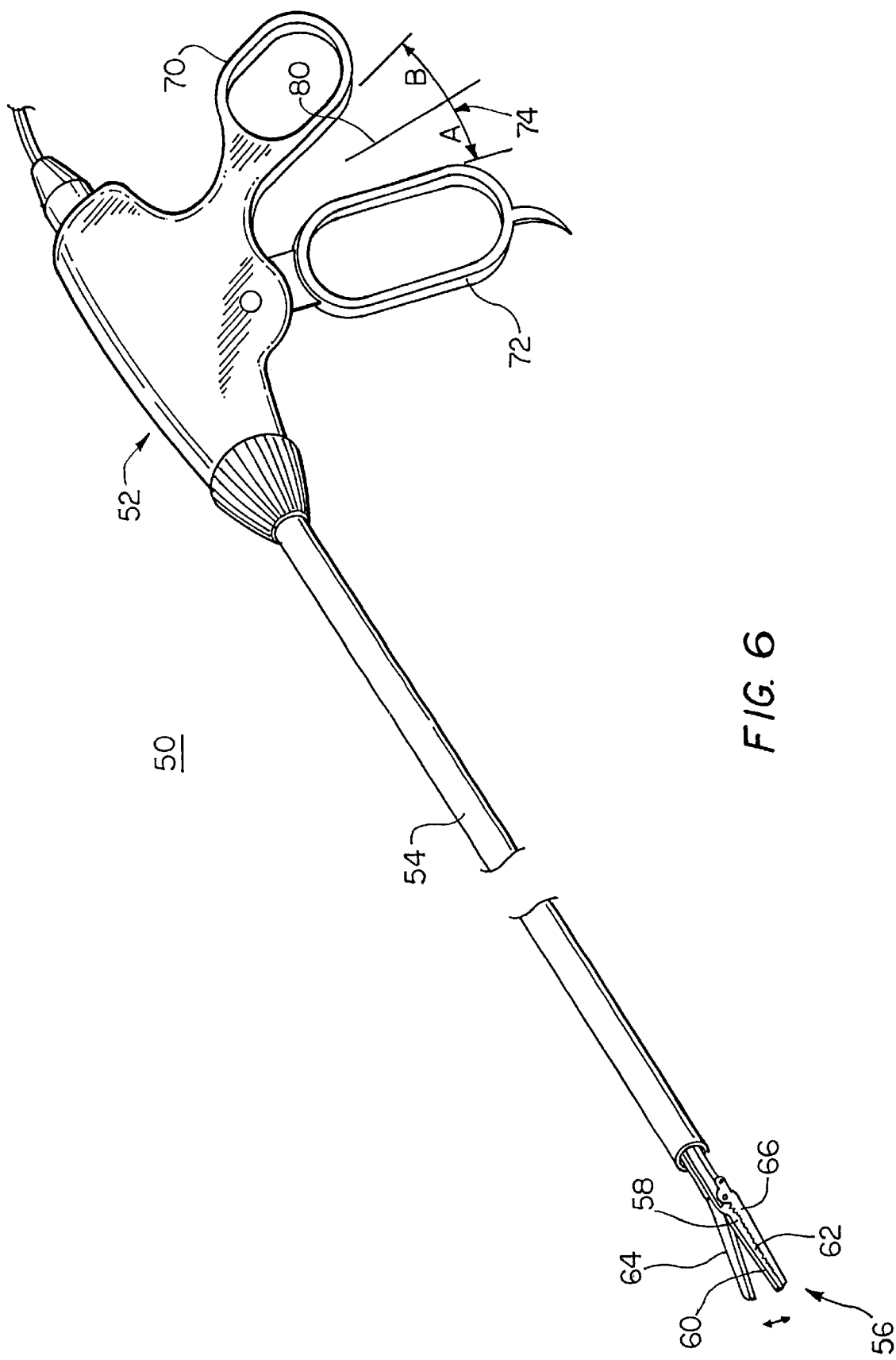
FIGS. 6–9 are schematic views similar to FIG. 5 showing the operation of the surgical instrument of the subject invention in both the tissue cutting and the tissue grasping modes.

Instead, and in accordance with one important feature of the subject invention, the surgeon grasps fixed scissor like handle 70 and pivoting handle 72, FIG. 6 with one hand, and is able to move pivoting handle 72 through a predetermined angular range of motion with respect to fixed handle 70 as shown by arrow 74. In an alternative embodiment, the pivoting handle could be handle 70 and the fixed handle could be handle 72.

Figure 7:
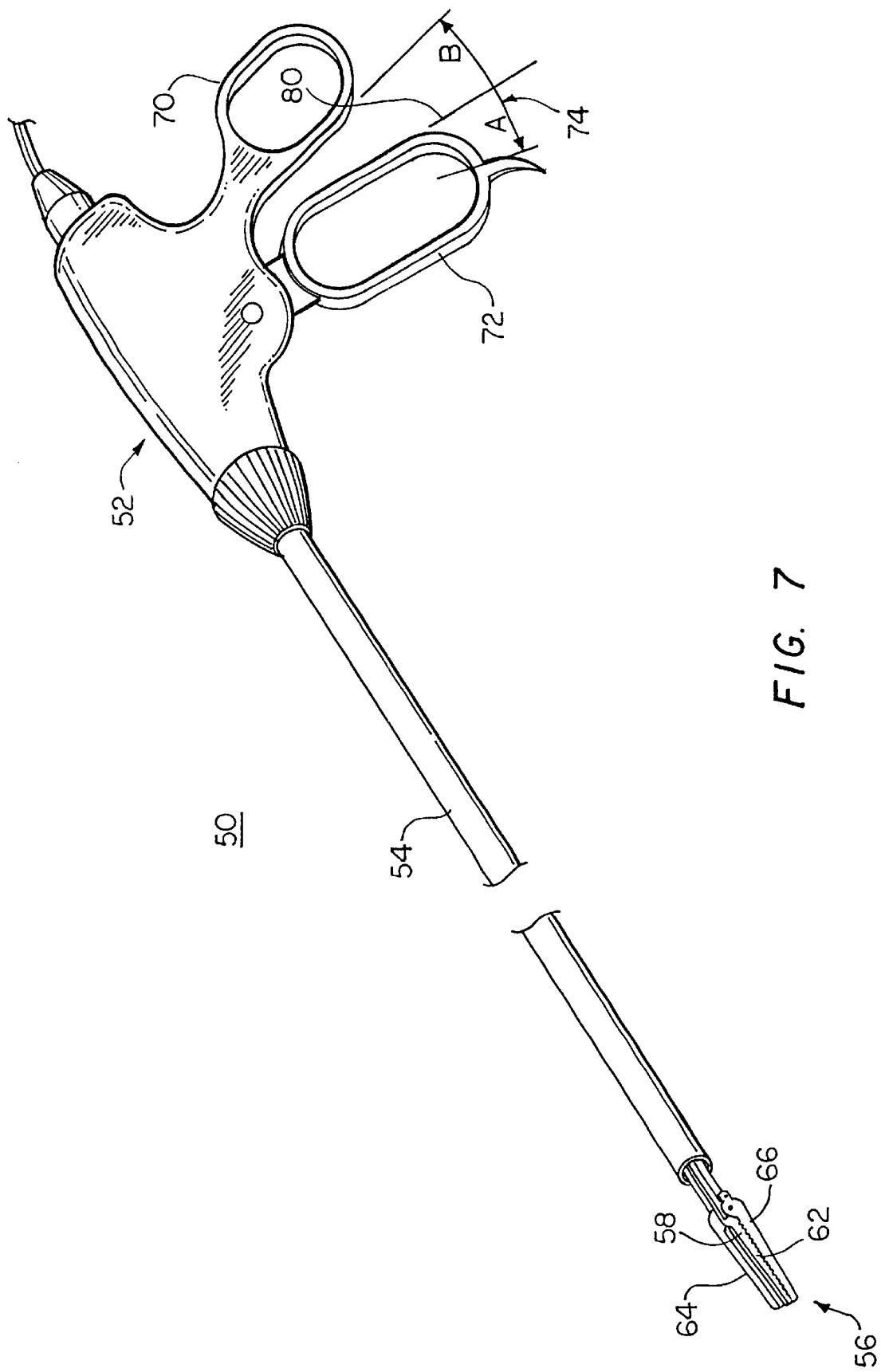

This complete angular range of motion is divided into two approximately equal portions A and B separated by dividing line 80 as shown in FIGS. 6–9. In angular motion range A, pivoting forcep jaw 66 remains closed against forcep jaw 62 and pivoting scissor blade 64 is fully opened when pivoting handle 72 is in the position shown in FIG. 6 and then fully closed when pivoting handle 72 is moved proximate the point where dividing line 80 intercepts arrow 74 as shown in FIG. 7.

Thus, in portion A of the angular range of motion of pivoting handle 72, scissor blades 64 and 60 open and close to perform tissue cutting operations.

Figure 8:
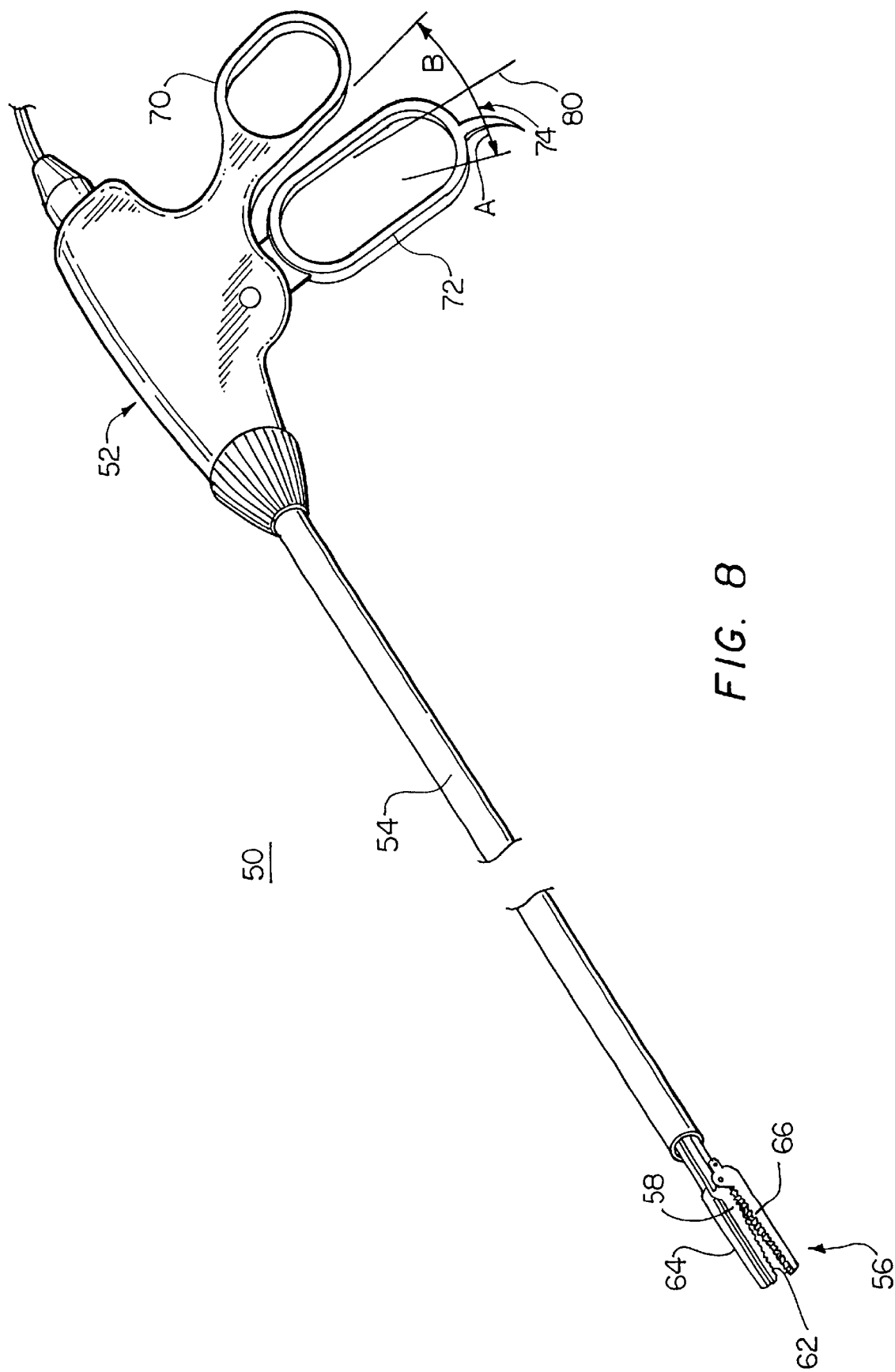
Figure 9:
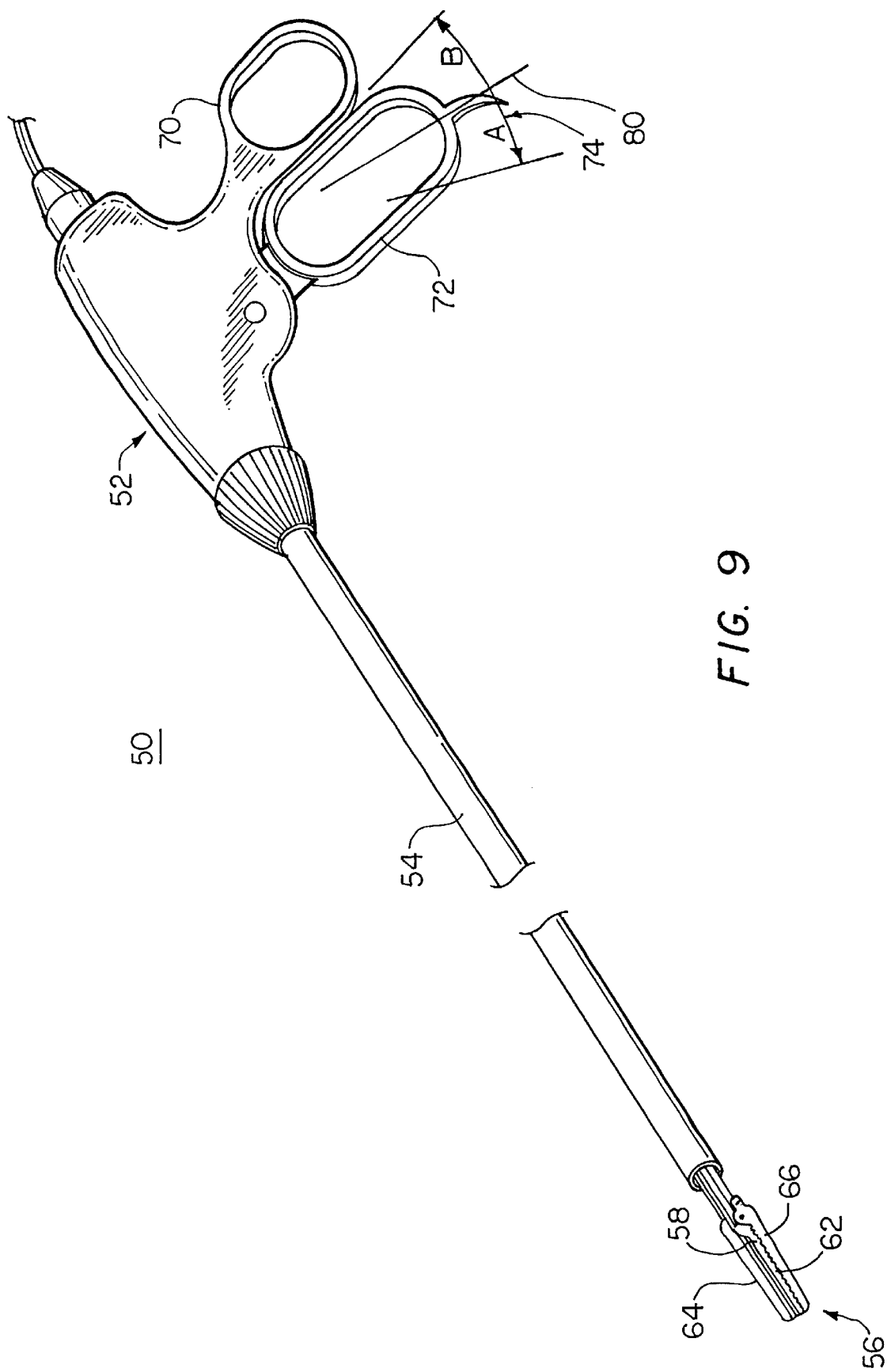

After pivoting handle 72 reaches the mid-point of its angular range of motion, pivoting scissor jaw 64 remains closed proximate fixed member 58 and pivoting forcep jaw 66 opens as shown in FIG. 8. When pivoting handle 72 is moved proximate fixed handle 70, pivoting forcep jaw 66 closes as shown in FIG. 9.

Thus, in portion B of the angular range of motion of pivoting handle 72, forcep jaws 62 and 66 open and close to perform tissue grasping procedures. In this way, the use of device 50 is intuitive, ergonomic, and even self-evident and operable by the surgeon in a way he or she expects without the need to actuate separate levers and the like in order to alternate between cutting and tissue grasping procedures.

Shaft 54, FIGS. 5–9, includes a linkage assembly including means for opening and closing scissor blades 64 and 60 during one portion (portion A in the figures) of the angular range of motion of pivoting handle 72 and for opening and closing forcep jaws 62 and 66 in a second portion (portion B in the figures) of the angular range of motion of pivoting handle 72.

Figure 10:
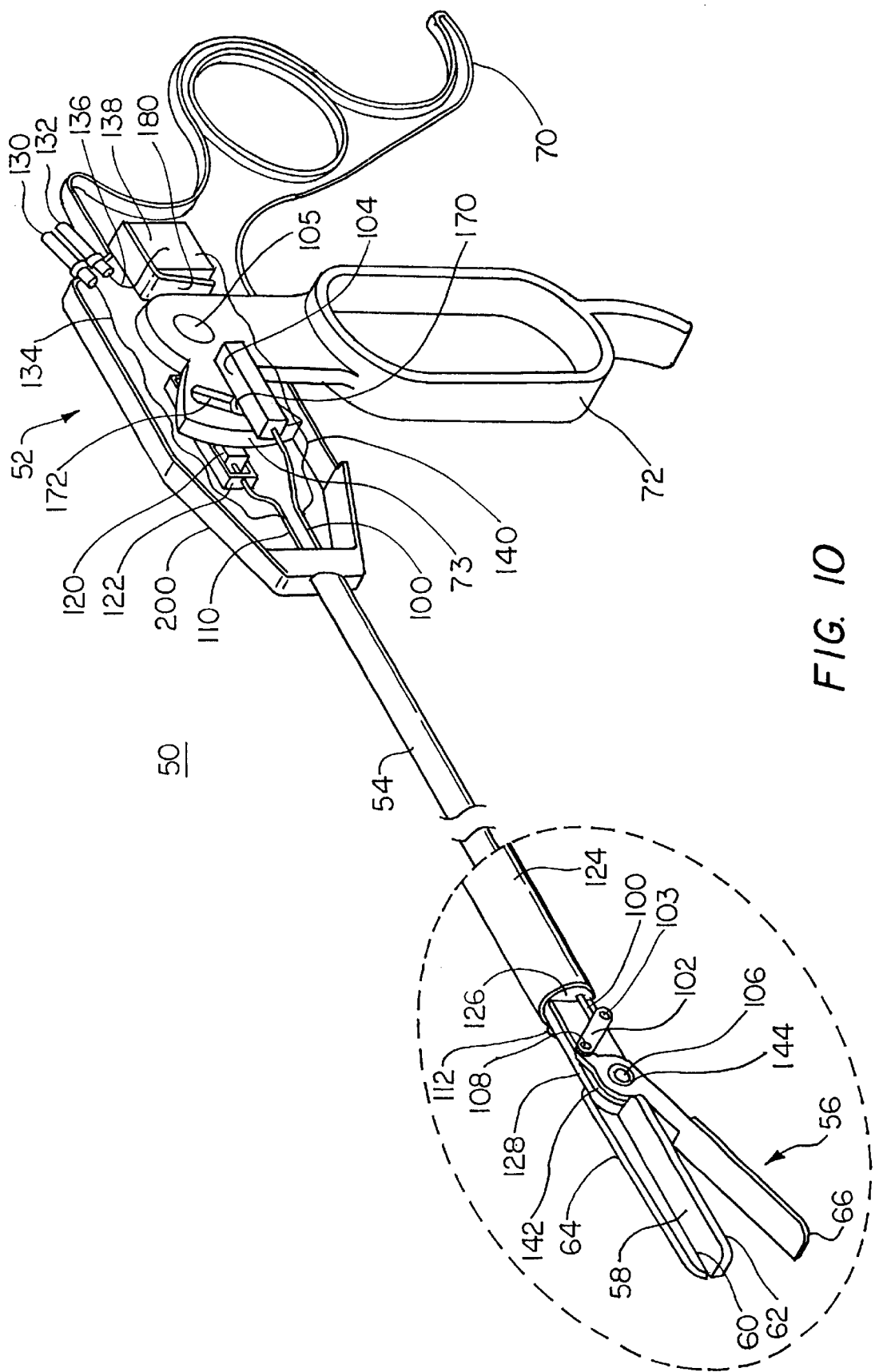
FIG. 10 is another schematic view of the surgical instrument of the subject invention showing the primary components thereof.

In the preferred embodiment, this linkage assembly includes forcep jaw push rod 100, FIG. 10 slidably disposed in shaft 54 and connected on one end to forcep jaw pivoting link 102 at pin 103 and connected on the other end to jaw block 104. Forcep jaw 66 pivots about hinge pin 106 and is connected to forcep jaw pivoting link 102 at pin 108. Pivoting link 102 is angled upward and to the left as shown in FIG. 10 such that its highest point is at pin 108.

The linkage assembly also includes scissor blade push rod 110 slidably disposed in shaft 54 and connected on one end to scissor blade pivoting link 112. Pivoting link 112 is angled down into the left as shown in drawing such that its highest point is at a pin (not shown) which connects scissor blade push rod 110 to pivoting link 112.

The other end of pivoting link 112 is pinned to the proximal end of scissor blade 64 which is pivotably attached to fixed member 58 by hinge pin 106. Scissor blade push rod 110 is connected on one end to scissor block 120 which is slidably disposed in race or channel 122 inside handle assembly 52.

Shaft assembly 54 typically includes outer tube 124 and disposed therein core element 126 which terminates in member 128 which itself forms fixed member 58. Core element 126 includes longitudinal orifices therethrough which receive forceps jaw push rod 100 and scissor blade push rod 110 in a sliding relationship. Scissor like handle 72 pivots about shaft 105 disposed in handle assembly 52.

As shown in FIG. 10, the proximal ends of the forcep jaw push rod 100 and scissors jaw push rod 110 are connected to forceps jaw block 104 and scissors block 120, respectively. Jaw block projections (as shown at 170 for jaw block 104) on the side of each of the forcep jaw block 104 and scissor block 120 engage with cam grooves as shown at 172 for jaw block 104 on opposite faces of ear 73 of pivoting handle 72. As pivoting handle 72 is rotated through its full range of motion, the jaw block projections are pushed either forward or back by the cam grooves. Up or down motion of the jaw blocks is prevented by races 122. Forward and back motion of forcep jaw block 104 and scissor block 120 causes the respective push rods to move forward and back which in turn causes forcep jaw 66 or scissor block 64 to open and close. The cam grooves are shaped so that when the pivoting handle is rotated through its full range of motion, the coordinated action of forceps jaw and scissor jaw operate as described above. Thus, scissor block 120 has a projection similar to jaw block 104 and the other side of handle 72 has a cam groove similar to groove 172. Moreover, jaw block 104 slides in a race similar to race 122.

In the preferred embodiment, instrument 50 is bipolar for coagulation procedures and includes RF energy connector pins 130 and 132 extending from handle assembly 52 as shown. Conductor 134 electrically connects connector pin 130 with centrally disposed fixed member 58 which is made of a conductive material. Conductor 136 electrically connects connector pin 132 with switch 138 and conductor 140 electrically connects switch 138 with forcep jaw push rod 100 which is also made of a conductive material.

Insulator plate 142 is disposed between forceps jaw 66 and fixed member 58 and insulating bushing 144 is disposed between hinge pin 106 and forceps jaw 106 to electrically isolate forcep jaw 66 from the other components of end assembly 56.

During surgery, tissue is coagulated by grasping a portion of the tissue between the forcep jaws and applying a radio frequency potential across the jaws of the forceps. This RF potential rapidly heats a very localized portion of the tissue between the forceps jaws. This rapid local heating by itself or combined with compressive forces exerted by the forceps jaws results in a sealing off of small blood vessels within the tissue through a combination of adhesion of the tissue comprising the vessels to itself and coagulation of the blood within the vessels.

Control of RF power to a laparoscopic instrument is usually controlled by a foot switch (not shown) connected to an RF generator which is in turn connected to the laparoscopic instrument. Since application of RF energy to the present invention is desired when the forceps are gripping tissue and not when the scissors are cutting tissue, contact safety switch 138 is provided. The safety switch opens when the handle 72 is within that range of its motion that causes the scissors to open and close (range A as described above). When the switch is open, no RF energy may be applied to the forceps jaw. The switch is closed when the handle 72 is within the range of its motion that causes the forceps jaws to open and close (Range B as described above). Opening and closing of the switch is accomplished by handle 72 pressing on contact 180 of switch 138.

A monopolar arrangement could also be employed in the instrument of the subject invention if desired whereby one component of device 50 would serve as one electrode and the second electrode is connected directly to the patient.

Figure 11:
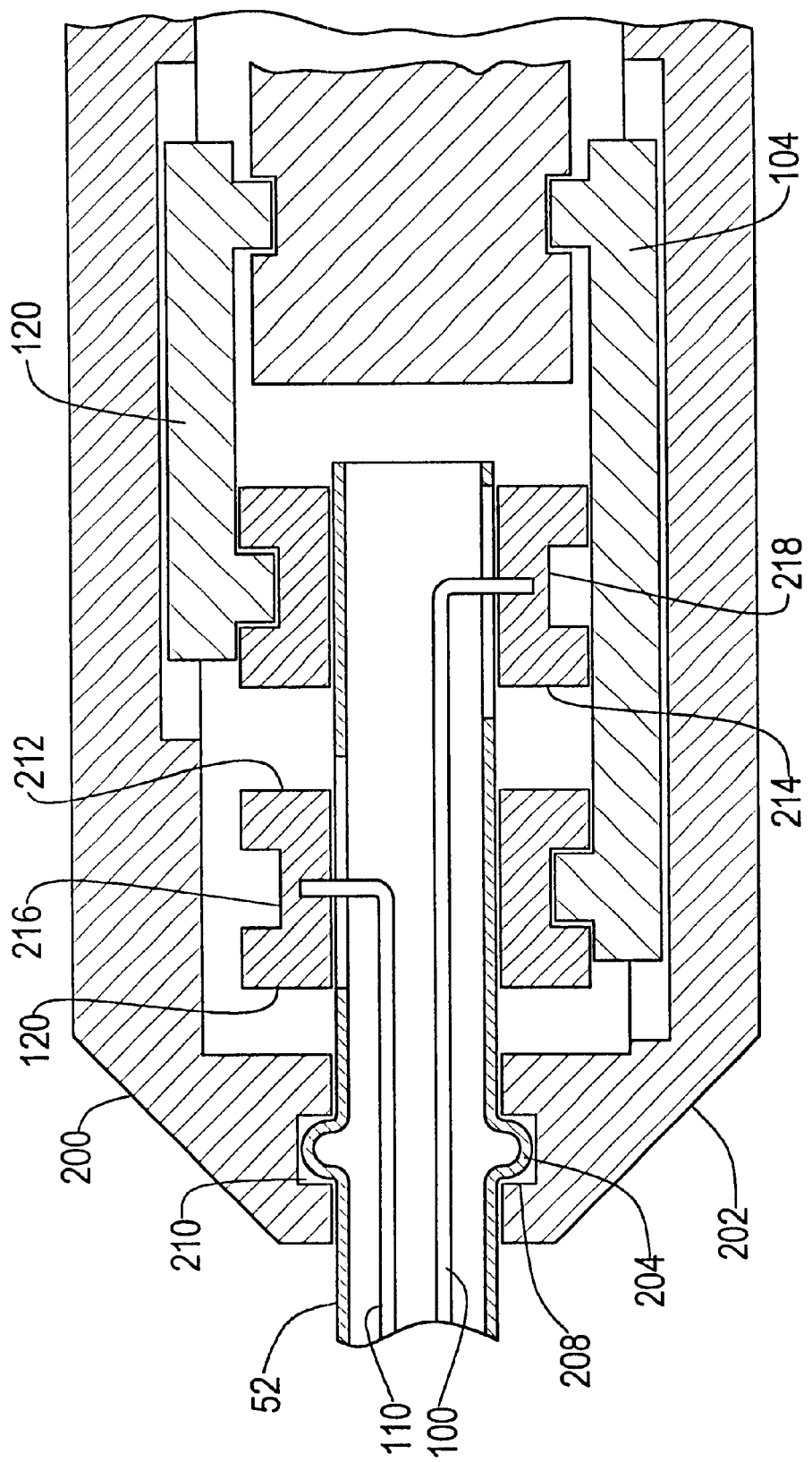
FIG. 11 is a schematic cross-sectional top view of the interior of the handle assembly of the surgical instrument shown in FIG. 10.

In one embodiment, shaft 52, FIG. 11 is rotatable. As such, there are means for rotating shaft 52 relative to handle assembly 52. Shaft 52 is captured between two halves 200, 202 of the handle body with enough clearance to allow the shaft to rotate. Flange 204 on the shaft prevents longitudinal motion of the shaft relative to the handle body. Scissors rod 110 and jaw rod 100 are bent 90 degrees as shown with the bent ends fitting through slots 208, 210 in the shaft. The bent ends then attach to scissors ring 212 and jaw ring 214, respectively. Both rings slide along the shaft. Circumferential grooves 216 and 218 in the rings couple with projections on the scissors block 120 and jaw block 104. These blocks are actuated by cam grooves in the movable handle 72. Their motion is constrained by races in the handle body. In this configuration, shaft 52, jaw and scissors rods 110 and 100 and the jaw and scissors rings 212 and 218 may rotate together relative to the handle body 200. The circumferential grooves in the rings allow the rings to rotate relative to the jaw block 104 or scissors block 120 but allow the jaw block or scissors block to move its respective ring longitudinally along the shaft and thereby actuate the jaw or scissors via the rods 110 and 100. Hence, this configuration allows the scissors or forceps jaw to be operated irrespective of the rotational position of the shaft (and associated components) relative to the handle. A rotator ring (not shown) may be fixed to the outside of the shaft just forward of the handle body to facilitate grasping and rotating the shaft.

Thus, surgical instrument 50 includes end assembly 56 with both a pivoting scissor blade 64 and a pivoting forcep jaw 66 thus eliminating the need for the surgeon to switch instruments during a given medical procedure and which also eliminates the need for additional cannulas inserted through a patient's abdominal wall. The scissoring and the grasping capabilities, however, are as good as available separately in single function devices. The operation of surgical instrument 50 is intuitive and the surgeon is not required to operate separate levers in order to switch between cutting and grasping procedures. Surgical instrument 50 is simple in design and can be manufactured at low cost. The surgeon is able to remain focused on the operating procedure and medical procedures are performed in a shorter period of time. Surgical instrument 50 is able to be received through a five millimeter cannula and can be easily and ergonomically operated by one hand. The surgical instrument of the subject invention can be easily equipped with bipolar or monopolar RF energy subsystems for electrosurgical procedures and moreover can be readily equipped with surgical end effectors other than scissors and tissue graspers such as scissors and clamps or bipolar coagulation devices and clamps. Other examples include scissor blades combined with graspers, dissectors, peanuts; bipolar graspers combined with forceps, dissectors, peanuts; peanuts combined with graspers, dissectors, and bipolar devices; and needle carriers combined with scissors, graspers, dissectors, and bipolar devices.

Surgical instrument 50 is intuitive to use, ergonomic, easier to use, and easier to manufacture than prior art devices. It allows surgeons to perform both tissue cutting and grasping procedures without the need to replace the end assembly. Instead, end assembly 56 incorporates both scissor and forcep jaws and features uniquely configured fixed central member 58 which functions both as a scissor blade and a forceps jaw disposed between separate pivotable scissor blade 64 and a separate pivotable forcep jaw 66. The linkage assembly, connected to the end assembly and scissor like grips 72 and 70 allow the surgeon to open and close scissor blades 64 and 60 in one scissor grip motion range and to open and close forcep jaws 62 and 66 in another scissor grip motion range.

Although specific features of the invention are shown in some drawings and not in others, however, this is for convenience only as each feature may be combined with any or all of the other features in accordance with the invention. Moreover, other embodiments will occur to those skilled in the art and are within the following claims:

What is claimed is:

1. A surgical instrument comprising:
   a handle assembly;
   a shaft connected on one end to the handle assembly; and
   an end assembly extending from the other end of the shaft, the end assembly including:
      a fixed member including on a first surface thereof a fixed scissor blade and on a second surface thereof a fixed forcep jaw,
      a pivotable scissor blade operatively disposed to cut tissue between the fixed scissor blade and the pivotable scissor blade, and
      a pivotable forcep jaw operatively disposed to grasp tissue between the fixed forcep jaw and the pivotable forcep jaw.

2. The surgical instrument of claim 1 in which both the fixed forcep jaw and the pivotable forcep jaw includes serrations thereon.

3. The surgical instrument of claim 1 in which the fixed member is disposed between the pivotable scissor blade and the pivotable forcep jaw.

4. The surgical instrument of claim 3 in which the pivotable scissor blade is disposed above the fixed member and the pivotable forcep jaw is disposed below the fixed member.

5. The surgical instrument of claim 4 in which the fixed forcep jaw is on a lower surface of the fixed member and the fixed scissor blade is disposed on an upper surface of the fixed member.

6. The surgical instrument of claim 1 in which the handle assembly includes spaced scissor-like handles, at least one said handle being pivotably attached to the handle assembly and having an angular range of motion with respect to the handle assembly.

7. The surgical instrument of claim 6 in which the shaft includes a linkage assembly having means for opening and closing the scissor blades during one portion of the angular range of motion of the pivoting handle and for opening and closing the forcep jaws during a second portion of the angular range of motion of the pivoting handle.

8. The surgical instrument of claim 6 in which said means includes a scissor blade push rod slidably disposed in the shaft and a forceps jaw push rod slidably disposed in the shaft.

9. The surgical instrument of claim 8 in which the pivotable scissor blade is pivotably attached on one side of the fixed member and the pivotable forcep jaw is pivotably attached on another side of the fixed member.

10. The surgical instrument of claim 9 in which the scissor blade push rod is connected on one end to a scissor blade link which is connected to the pivotable scissor blade and in which the forcep jaw push rod is connected on one end to a forcep jaw link which is connected to the pivotable forcep jaw.

11. The surgical instrument of claim 8 in which the scissor blade push rod is connected on one end to a scissor block slidably disposed in the handle assembly, the scissor block including a projection extending into a first cam groove, and in which the jaw push rod is connected on one end to a jaw block slidably disposed in the handle assembly, the jaw block including a projection extending into a second cam groove.

12. The surgical instrument of claim 1 further including electrical conductors connected on one end to the pivotable scissor blade and the pivotable forcep jaw for coagulating tissue.

13. The surgical instrument of claim 1 further including means for rotating the shaft relative to the handle assembly.

14. A surgical device comprising:
   a handle assembly;
   a shaft connected on one end to the handle assembly; and
   an end assembly extending from the other end of the shaft, the end assembly including:
      a fixed member including on one surface thereof a fixed portion of a first surgical instrument and on another surface thereof a fixed portion of a second surgical instrument,
      a pivotable portion of the first surgical instrument pivotably attached to the fixed member and disposed to cooperate with the fixed portion of the first surgical instrument to perform a first type of medical procedure, and
      a pivotable portion of the second surgical instrument pivotably attached to the fixed member and disposed to cooperate with the fixed portion of the second surgical instrument to perform a second type of medical procedure.

15. The surgical device of claim 14 in which the fixed portion of the first surgical instrument is fixed scissor blade and the pivotable portion of the first surgical instrument is a pivotable scissor blade.

16. The surgical device of claim 14 in which the fixed portion of the second surgical instrument is a fixed forcep jaw and the pivotable portion of the second surgical instrument is a pivotable forcep jaw.

17. An end assembly for a surgical instrument, the end assembly comprising:
   a fixed member including on one surface thereof a fixed scissor blade and on another surface thereof a fixed forcep jaw;
   a pivotable scissor blade pivotably attached to the fixed member for cutting tissue between the fixed scissor blade and the pivotable scissor blade; and
   a pivotable forcep jaw pivotably attached to the fixed member for grasping tissue between the fixed forcep jaw and the pivotable forcep jaw.

* * * * *

UNITED STATES PATENT AND TRADEMARK OFFICE
CERTIFICATE OF CORRECTION

PATENT NO.    : 6,358,268 B1
DATED         : March 19, 2002
INVENTOR(S)   : Hunt et al.

It is certified that error appears in the above-identified patent and that said Letters Patent is hereby corrected as shown below:

Column 9,
Line 44, please replace "6" with -- 7 --.

Signed and Sealed this

Twelfth Day of November, 2002

Attest:

Attesting Officer

JAMES E. ROGAN
Director of the United States Patent and Trademark Office